US006146732A

United States Patent [19]
Davis et al.

[11] Patent Number: 6,146,732
[45] Date of Patent: *Nov. 14, 2000

[54] THERMAL PACK HAVING A PLURALITY OF INDIVIDUAL HEAT CELLS

[75] Inventors: Leane Kristine Davis, Milford; Ronald Dean Cramer; William Robert Ouellette, both of Cincinnati; Dawn Michele Kimble, Sharonville, all of Ohio

[73] Assignee: The Procter & Gamble Company, Mason, Ohio

[*] Notice: This patent is subject to a terminal disclaimer.

[21] Appl. No.: 08/984,009

(List continued on next page.)

[22] Filed: Dec. 3, 1997

Related U.S. Application Data

[63] Continuation-in-part of application No. 08/777,853, Dec. 31, 1996, Pat. No. 6,020,040.
[51] Int. Cl.[7] ...................................................... A61F 7/00
[52] U.S. Cl. .......................... 428/64.1; 62/53; 126/204; 126/263.02; 252/67; 252/70; 428/66.4; 428/66.6; 428/68; 428/914; 607/1; 607/4
[58] Field of Search .......................... 428/64.1, 68, 66.4, 428/66.6, 914; 126/263.02, 204; 62/53; 252/67, 70; 607/114

[56] References Cited

U.S. PATENT DOCUMENTS

| Re. 32,026 | 11/1985 | Yamashita et al. | 126/263 |
|---|---|---|---|
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,516,564 | 5/1985 | Koiso et al. | 126/263 |
| 4,522,190 | 6/1985 | Kuhn et al. | 126/263 |
| 4,575,097 | 3/1986 | Brannigan et al. | 128/402 |
| 4,649,895 | 3/1987 | Yasuki et al. | 126/263 |
| 4,756,299 | 7/1988 | Podella | 126/263 |
| 4,860,748 | 8/1989 | Chiurco et al. | 128/399 |
| 4,886,063 | 12/1989 | Crews | 128/403 |
| 4,925,743 | 5/1990 | Ikeda et al. | 428/702 |
| 4,995,126 | 2/1991 | Matsuda | 5/421 |
| 5,025,777 | 6/1991 | Hardwick | 126/263 |
| 5,046,479 | 9/1991 | Usui | 126/204 |
| 5,062,269 | 11/1991 | Siegel | 62/4 |
| 5,125,392 | 6/1992 | Hardwick | 126/263 |
| 5,179,944 | 1/1993 | McSymytz | 128/403 |
| 5,190,033 | 3/1993 | Johnson | 128/403 |
| 5,233,981 | 8/1993 | Miyashita | 607/114 |
| 5,342,412 | 8/1994 | Ueki | 607/114 |
| 5,366,491 | 11/1994 | Ingram et al. | 607/108 |
| 5,366,492 | 11/1994 | Ueki | 607/114 |
| 5,405,671 | 4/1995 | Kamin et al. | 428/69 |

FOREIGN PATENT DOCUMENTS

| 0 370 600 A1 | 7/1989 | European Pat. Off. . |
|---|---|---|
| 160443 | 9/1983 | Indonesia . |
| 56-145846 | 11/1981 | Japan . |
| 57-170252 | 10/1982 | Japan . |
| 58-37075 | 3/1983 | Japan . |
| 3-100090 | 4/1991 | Japan . |
| 5-317188 | 12/1993 | Japan . |
| 6-1969 | 1/1994 | Japan . |
| 6-315498 | 11/1994 | Japan . |
| 6-343658 | 12/1994 | Japan . |
| 7-67907 | 3/1995 | Japan . |
| 7-124192 | 5/1995 | Japan . |
| 7-49042 | 5/1995 | Japan . |
| 7-194641 | 8/1995 | Japan . |
| 7-194642 | 8/1995 | Japan . |
| 8-98856 | 4/1996 | Japan . |
| 8-126656 | 5/1996 | Japan . |
| 2 205 496 | 12/1988 | United Kingdom . |
| 2 297 490 | 8/1996 | United Kingdom . |
| WO 94/00087 | 1/1994 | WIPO . |

OTHER PUBLICATIONS

U.S. application No. 08/777,830, Cramer et al., filed Dec. 31, 1996.
U.S. application No. 08/775,210, Cramer et al., filed Dec. 31, 1996.
U.S. application No. 08/777,642, Cramer et al., filed Dec. 31, 1996.
U.S. application No. 08/777,856, Cramer et al., filed Dec. 31, 1996.
U.S. application No. 08/496,565, Ouellette et al., filed Jun. 29, 1995.
U.S. application No. 08/748,203, Ouellette et al., filed Nov. 11, 1996.
U.S. application No. 08/496,716, Burkett et al., filed Jun. 29, 1995.

(List continued on next page.)

*Primary Examiner*—Nasser Ahmad
*Attorney, Agent, or Firm*—Loy M. White; Douglas C. Mohl

[57] ABSTRACT

The present invention relates to disposable thermal packs comprising a unified structure having at least one continuous layer of a semirigid material which softens when heated. The thermal packs also comprise a plurality of individual heat cells, which typically comprise an exothermic composition, spaced apart and fixed throughout the unified structure. The material of the continuous layer or layers provide sufficient rigidity to maintain structural support of the heat cells, to prevent unacceptable stretching of structures of the continuous layer or layers during processing or use of the thermal packs, and to deter easy access to heat cell contents, while also providing good overall drape characteristics when heated. The thermal packs, when incorporated into body wraps, pads, and the like, provide efficient and effective heat coverage by having excellent conformity with various body forms.

38 Claims, No Drawings

OTHER PUBLICATIONS

U.S. application No. 08/746,359, Burkett et al., filed Nov. 11, 1996.
U.S. application No. 08/496,373, Ouellette et al., filed Jun. 29, 1995.
U.S. application No. 08/686,800, Ouellette et al., filed Jul. 26, 1996.
U.S. application No. 08/672,166, Viltro et al., filed Jun. 26, 1996.
U.S. application No. 08/754,947, Burkett et al., filed Nov. 21, 1996.
U.S. application No. 08/623,752, White, filed Mar. 29, 1996.
U.S. application No. 08/777,853, Cramer et al., filed Dec. 31, 1996.
U.S. application No. 08/680,472, Ouellette et al., filed Jul. 15, 1996.
U.S. application No. 08/984,365, Davis et al., filed Dec. 3, 1997.
U.S. application No. 08/984,366, Davis et al., filed Dec. 3, 1997.
U.S. application No. 08/984,405, Davis et al., filed Dec. 3, 1997.
U.S. application No. 08/984,367, Davis et al., filed Dec. 3, 1997.
U.S. application No. 08/916,083, Davis et al., filed Aug. 21, 1997.
U.S. application No. 08/915,831, Barone et al., filed Aug. 21, 1997.
U.S. application No. 08/916,094, Davis et al., filed Aug. 21, 1997.

THERMAL PACK HAVING A PLURALITY OF INDIVIDUAL HEAT CELLS

CROSS REFERENCE TO RELATED APPLICATION

This is a continuation-in-part of application Ser. No. 08/777,853, filed on Dec. 31, 1996, now U.S. Pat. No. 6,020,040.

TECHNICAL FIELD

The present invention relates to a disposable thermal pack comprising a unified structure having at least one continuous layer and a plurality of individual heat cells, which typically comprise an exothermic composition, spaced apart and fixed within or to the unified structure of the thermal pack. The continuous layer or layers preferably comprise a semirigid material which softens when heated. The semirigid material provides sufficient rigidity to maintain structural support of the heat cells, to prevent unacceptable stretching of structures of the continuous layer or layers during processing or use of the thermal pack, and/or to deter easy access to the heat cell contents, while also providing good overall drape characteristics when heated. The thermal pack, when incorporated into body wraps, pads, and the like, provides efficient and effective heat coverage by having excellent conformity with various body forms.

BACKGROUND OF THE INVENTION

A common method of treating acute, recurrent, and/or chronic pain is by the topical application of heat to the afflicted area. Such heat treatments are used as a means of therapy for conditions which include aches, stiffness in muscles and joints, nerve pain, rheumatism and the like. Typically, the method for relieving pain using heat treatments has been to topically apply a relatively high heat, i. e., greater than about 40° C., for a short period of time, i. e., from about twenty minutes to about one hour. These treatments include the use of whirlpools, hot towels, hydrocollators, hot water bottles, hot packs, and electric heating pads. Many of these devices employ reusable thermal packs containing, e.g., water and/or microwaveable gels. In general, most of these devices are inconvenient to use. Further, many of these thermal units or devices do not provide long lasting heat and also do not maintain a consistent temperature over long periods of time. The beneficial therapeutic effects from this administration of heat diminish after the heat source is removed.

The present inventors, however, have discovered that maintaining a sustained skin temperature of from about 32° C. to about 50° C., preferably from about 32° C. to about 45° C., more preferably from about 32° C. to about 42° C., most preferably from about 32° C. to about 39° C., still most preferably from about 32° C. to about 37° C. for a period of from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved without any adverse events, such as skin burns which may be incurred by using a high temperature for a long period of time, substantially relieves acute, recurrent, and/or chronic pain, including skeletal, muscular, and/or referred pain, of a person having such pain.

The present inventors have further discovered that preferably maintaining a sustained skin temperature of from about 32° C. to about 43° C., preferably from about 32° C. to about 42° C., more preferably from about 32° C. to about 41° C., most preferably from about 32° C. to about 39° C., still more preferably from about 32° C. to about 37° C., for a time period of greater than about 1 hour, preferably greater than about 4 hours, more preferably greater than about 8 hours, even more preferably greater than about 16 hours, most preferably about 24 hours, substantially relieves acute, recurrent, and/or chronic pain, including skeletal, muscular, and/or referred pain, of a person having such pain and substantially prolongs relief even after the heat source is removed from the afflicted body part.

Disposable heat packs based on iron oxidation, such as those described in U.S. Pat. Nos. 4,366,804, 4,649,895, 5,046,479 and Re. 32,026, are known and can provide long-lasting heat. However, such devices have proven not totally satisfactory because many of these devices cannot maintain a consistent and controlled temperature and/or such thermal devices are bulky and have unsatisfactory physical dimensions which hinder their effectiveness. Specifically, such devices cannot be easily incorporated into wraps which can comfortably conform to various body contours, and hence, they deliver short duration, inconsistent, inconvenient and/or uncomfortable heat application to the body.

The present inventors have discovered that the use of thin, flexible materials and a plurality of individual heat cells spaced apart for their thermal packs improves temperature control and overcomes many of the past difficulties, but has introduced some new difficulties. Though inherently more flexible, thinner materials, when combined with a plurality of individual heat cells, can lead to difficulty retaining sufficient rigidity to maintain structural support of the heat cells, preventing unacceptable stretching of structures of the thin, flexible material during processing or use, and/or deterring easy access to the heat cell contents.

The present inventors have similarly discovered that the use of thin but overly rigid materials, and a plurality of individual heat cells spaced apart for their thermal pack, improves temperature control, alleviates unacceptable stretching of the material during processing or use, restores structural support of the heat cells, and deters easy access to the heat cell contents. However, thermal packs made of the thin but overly rigid material do not drape well around various body parts, even when heated, leading to a less than optimal comfortable application of heat to the body. That is, thermal packs made of overly rigid materials conform poorly to body locations, particularly body locations which require the material to bend and conform in three dimensions during use.

The present inventors have overcome these difficulties by developing disposable thermal packs, which possess some or all of the desired properties of both the thin, flexible materials and the thin, overly rigid materials mentioned above, comprising at least one continuous layer of a material which is sufficiently rigid in specific areas of the thermal packs, yet which softens in between such areas during use, most preferably comprising a semirigid coextruded material of polypropylene and ethylene vinyl acetate copolymer (EVA), together with a plurality of individual heat cells, having an exothermic composition, preferably comprising a specific iron oxidation chemistry and having specific physical dimensions and fill characteristics, spaced apart and fixed within or to the unified structure of the thermal pack. Active heat cells, that is, heat cells having a temperature of about 35° C. or greater, preferably soften narrow portions of the continuous layer or layers of semirigid material which immediately surround the heat cells. Any remaining portions of the continuous layer or layers which surround the softened portions preferably remain more rigid. The narrow, softened portions act as hinges between the heat cells and between any remaining, cooler, more rigid portions, bending preferentially more than either the heat cells or more rigid portions. This results in thermal packs which possess sufficient rigidity to maintain structural support of the heat cells, to prevent unacceptable stretching of structures of the continuous layer or layers during processing or use, and to deter easy access to the heat cell contents, while still maintaining good overall drape characteristics when heated. The thermal packs, when incorporated into body wraps, pads, and the like, provide efficient and effective heat coverage by having excellent conformity with various body forms.

The present inventors have also discovered that it may be desirable to selectively place heat cells into positions fixed within or to the unified structure of the thermal pack, relative to each other which are sufficiently close so as to block some or all possible axes, which otherwise would have passed uninterrupted between the heat cells, through the thermal pack, or select regions thereof, to minimize or eliminate undesirable, uninterrupted fold lines, and/or to increase the structural support that the heat cell matrix imparts to the thermal pack. That is, placement of the heat cells into positions relative to each other which are sufficiently close to block some or all possible axes which would otherwise have passed uninterrupted, between the heat cells, causes the disposable thermal packs of the present invention to fold along a multiplicity of short interconnected fold lines oriented in a number of different directions relative to each other. Folding along a multiplicity of interconnected fold lines results in good overall drape characteristics.

It is therefore an object of the present invention to provide disposable thermal packs which comprise a unified, structure having at least one continuous layer, preferably of a semirigid material which has different stiffness characteristics over a range of temperatures, and a plurality of individual heat cells, which provide a controlled and sustained temperature and which reach their operating temperature range relatively quickly. The heat cells are spaced apart and fixed within or to the unified structure of the disposable thermal pack.

It is also an object of the present invention to provide thermal packs which can be easily incorporated into disposable body wraps, having good overall drapability while maintaining sufficient rigidity to maintain structural support of the heat cells, to prevent unacceptable stretching of the continuous layer or layers during processing or use, and/or deter easy access to the heat cell contents.

It is a further object of the present invention to provide thermal packs which adapt to a wide variety of body contours by possessing at least two dimensional drape characteristics across the thermal pack to provide consistent, convenient and comfortable heat application.

It is a still further object of the present invention to provide methods of treating acute, recurrent, and/or chronic pain, including skeletal, muscular, and/or referred pain, of a person having such pain, by maintaining a sustained skin temperature of from about 32° C. to about 50° C. for a period of time of from about twenty seconds to about twenty-four hours, preferably by maintaining a skin temperature of from about 32° C. to about 43° C. for a time period of greater than about 1 hour to provide prolonged relief from such pain.

These objectives and additional objectives will become readily apparent from the detailed description which follows.

SUMMARY OF THE INVENTION

The disposable thermal packs of the present invention comprise a unified structure having at least one continuous layer of a material, preferably which is semirigid at a temperature of about 25° C., having a tensile strength of about 0.7 g/mm$^2$ or greater, and at least two-dimensional drape, and which is substantially less rigid at a temperature of 35° C. or greater, having a tensile strength substantially less than the tensile strength of the material at about 25° C.

The continuous layer or layers of material of the present invention preferably comprise a coextruded material, more preferably a coextruded material comprising polypropylene, most preferably a coextruded material wherein a first side comprises polypropylene and a second side comprises a tie-layer of a low melt temperature polymer, preferably EVA, preferably having a combined basis weight thickness of less than about 50 μm.

The disposable thermal packs of the present invention further comprise a plurality of individual heat cells, which preferably comprise an exothermic composition, more preferably comprising an iron oxidation chemistry, spaced apart and fixed within or to the unified structure of the disposable thermal pack.

The heat cells may be placed into positions fixed within or to the unified structure of the thermal pack, relative to each other and sufficiently close so that some or all of the possible axes that would otherwise pass uninterrupted between the heat cells are blocked by the heat cells to cause the thermal packs to fold along a multiplicity of short interconnected fold lines.

The present invention further comprises methods of treating acute, recurrent, and/or chronic pain, including skeletal, muscular, and/or referred pain, of a person having such pain, by maintaining a sustained skin temperature of from about 32° C. to about 50° C. for a period of time of from about twenty seconds to about twenty-four hours, preferably by maintaining a skin temperature of from about 32° C. to about 43° C. for a time period of greater than about 1 hour, more preferably by applying the disposable thermal packs of the present invention to the afflicted body part, to provide prolonged relief from such pain.

All percentages and ratios used herein are by weight of the total composition, and all measurements made at 25° C., unless otherwise specified.

DETAILED DESCRIPTION OF THE INVENTION

The thermal packs of the present invention comprise at least one continuous layer of a material, which preferably exhibits specific thermophysical properties and a plurality of individual heat cells, which preferably comprise an exothermic composition, spaced apart and fixed within or to the structure of the disposable thermal pack.

The material of the at least one continuous layer is preferably semirigid when at room temperature, i.e., about 25° C., or below, but softens and becomes substantially less rigid when heated to about 35° C. or greater. Therefore, when heat cells, which are fixed within or to the unified structure of the thermal pack, are active, that is at a heat cell temperature of from about 35° C. to about 60° C., preferably from about 35° C. to about 50° C., more preferably from about 35° C. to about 45° C., and most preferably from about 35° C. to about 40° C., the narrow portion of the continuous layer or layers of material immediately surrounding each heat cell preferably softens and acts as a hinge between the heat cells and remaining more rigid portions of the continuous layer or layers, bending preferentially more than either the heat cells or cooler, more rigid portions. This results in a thermal pack which possesses sufficient rigidity to maintain structural support of the heat cells and prevent unacceptable stretching of structures of the continuous layer or layers during processing or use, while still maintaining good overall drape characteristics when heated. The thermal packs of the present invention, preferably when incorporated into body wraps, pads, and the like which easily adapt to a wide variety of body contours, provides consistent, convenient, and comfortable heat application, and an excellent conformity with body forms, while retaining sufficient rigidity to deter easy access to the heat cell contents.

"Disposable", as used herein, means that, while the thermal packs of the present invention may be stored in a resealable, substantially air-impermeable container and reapplied to the user's body as often as required for the relief of pain, they are intended to be thrown away, i. e., deposited in a suitable trash receptacle, after the heat source, i. e., the heat cell(s) have been fully expended.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Plurality of heat cells", as used herein, means more than one, preferably more than two, more preferably more than three, most preferably more than four, heat cells.

"Agglomerated pre-compaction composition", as used herein, means the mixture of dry powdered ingredients, comprising iron powder, carbonaceous powder, metal salt(s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Rigid", as used herein, means the property of a material wherein the material may be flexible, yet is substantially stiff and unyielding, and which does not form fold lines in response to gravitational pull or other modest forces.

"Semirigid material", as used herein, means a material which is rigid to some degree or in some parts, i. e., having at least two-dimensional drape at a temperature of about 25° C., and exhibits a toughness to maintain structural support of the heat cells in an unsupported format, and/or to prevent unacceptable stretching of structures of the material during processing or use and/or to deter easy access to heat cell contents while still maintaining good overall drape characteristics when heated.

"Two dimensional drape", as used herein, means drape which occurs across a continuous layer or layers, across a thermal pack, or across a select region of a layer or layers, or thermal pack, exclusively along one axis, i.e., one fold line forms, at the expense of other fold lines in response to gravitational pull or other modest forces.

"Three dimensional drape", as used herein, means drape which simultaneously occurs across a continuous layer or layers, across a thermal pack, or across a select region of a layer or layers, or thermal pack, along two or more axes, i. e., two or more fold lines form, in response to gravitational pull or other modest forces.

"Fold lines", as used herein, means the line along which a material forms a temporary or permanent crease, ridge, or crest in response to gravitational pull or other modest forces.

Continuous Layer(s)

The thermal packs of the present invention comprise at least one continuous layer of a material, which preferably exhibits specific thermophysical properties. Therefore, when heat cells, which are fixed within or to the unified structure of the thermal pack, are active, that is at a heat cell temperature of from about 35° C. to about 60° C., preferably from about 35° C. to about 50° C., more preferably from about 35° C. to about 45° C., and most preferably from about 35° C. to about 40° C., the narrow portion of the continuous layer or layers of material immediately surrounding each heat cell softens and acts as a hinge between the heat cells and between any remaining more rigid portion of the continuous layer or layers, bending preferentially more than either the heat cells or any cooler, more rigid portions. This provides good overall drape characteristics and an excellent conformity with body forms when heated, while maintaining structural support of the heat cells and/or preventing unacceptable stretching of structures of the continuous layer or layers during processing or use.

The continuous layer or layers of the present invention preferably comprises a material which is semirigid at a temperature of about 25° C. and which softens, i.e., becomes substantially less rigid, at a temperature of about 35° C. or greater. That is, the material of the present invention has a tensile strength, within the elastic deformation range of the material, of about 0.7 g/mm$^2$ or greater, preferably about 0.85 g/mm² or greater, more preferably about 1 g/mm² or greater, at about 25° C. and a tensile strength substantially less at about 35° C. or greater. "Substantially less", as used herein, means that the tensile strength of the material at about 35° C., or greater, is statistically significantly less than the tensile strength at about 25° C., at an appropriate statistical confidence (i. e., 95%) and power (i. e., ≧90%).

Typically, the tensile strength is measured using a simple tensile test on an electronic tensile test apparatus, such as a universal constant rate elongation tensile testing machine with computer, Instron Engineering Corp., Canton, Mass. Any standard tensile test may be used, for example, material samples are cut into strips having a width of about 2.54 cm (about 1 inch) and a length of from about 7.5 cm to about 10 cm (about 3 to about 4 inches). The ends of the strips are placed into the jaws of the apparatus with enough tension to eliminate any slack, but without loading the load cell. The temperature of the sample is then allowed to stabilize at the desired test temperature. The load cell of the apparatus is set for about 22.7 kg (50 pound) load, the elongation set for 5 mm, and the crosshead speed is set for about 50 cm/min. The apparatus is started and the tensile strength data is collected by the computer. The sample is then removed from the apparatus.

The tensile strength may be calculated as the slope of the tensile load vs. the extension during elastic deformation of the materials using the equation:

$$m=(L/E)$$

Where m=the slope in g/mm² during elastic deformation; L=the load at extension in g/mm; and E=the extension in mm.

The continuous layer or layers of the present invention also preferably comprises at least two-dimensional drape at about 25° C., i. e., a single fold or crease occurs in the material along a single axis, and preferably three-dimensional drape at about 35° C. or greater, i. e., two or more folds or creases occur along multiple axes. Drape may be determined by placing and centering a square sample, for example about 30 cm by about 30 cm (about 12 inches by about 12 inches), of material on the end of a cylindrical shaft with a pointed end, allowing the material to drape due to gravitational forces, and the number of fold lines counted. Materials that exhibits one-dimensional drape, i. e., have no folds or creases in any direction, are determined to be rigid, while materials that exhibit at least two-dimensional drape, i. e., have at least one fold or crease line forming along at least one axis, are determined to be semirigid.

Different materials may be capable of satisfying the specified requirements described above provided that the thickness is adjusted accordingly. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof These materials may be used alone, preferably extruded, more preferably coextruded, most preferably coextruded with a low melt temperature polymer including, but not limited to, ethylene vinyl acetate copolymer, low density polyethylene, and mixtures thereof.

The continuous layer or layers of material of the present invention preferably comprises polypropylene, more preferably a coextruded material comprising polypropylene, most preferably a coextruded material wherein a first side comprises polypropylene, preferably from about 10% to about 90%, more preferably from about 40% to about 60%, of the total thickness of the material, and a second side comprises a tie-layer of a low melt temperature copolymer, preferably EVA. The continuous layer or layers of material preferably comprise a combined basis weight thickness of less than about 50 μm, more preferably less than about 40 μm, most preferably less than about 30 μm.

A particularly suitable and preferred material for the continuous layer or layers of the present invention is a coextruded material having a first side of polypropylene and a second side of EVA having a total material thickness of from about 20 μm to about 30 μm, preferably about 25 μm (1 mil), wherein the polypropylene comprises about 50% and the EVA tie-layer comprises about 50% of the total material thickness. This material is available from Clopay Plastic Products, Cincinnati, Ohio, as P18-3161. When the polypropylene/EVA coextruded material is used to make the thermal packs and/or heat cells of the present invention, the polypropylene side is oriented to the outside (i.e., away from the exothermic composition).

Good overall drape characteristics and/or excellent conformity with various body forms, and/or increased structural support to the thermal pack, may also be achieved by selectively placing the heat cells into positions fixed within or to the unified structure of the thermal packs relative to each other which are sufficiently close so as to block some or all possible axes across the material of the continuous layer or layers which otherwise would have passed uninterrupted between the heat cells, through the thermal packs, or select regions thereof, to minimize or eliminate undesirable, uninterrupted fold lines. That is, placement of the heat cells into positions relative to each other which are sufficiently close so that the number of axes which pass uninterrupted, between the heat cells, is selectively controlled, such that the continuous layer or layers of the disposable thermal packs, or select regions thereof, preferably folds along a multiplicity of short interconnected fold lines oriented in a number of different directions relative to each other. Folding along a multiplicity of interconnected fold lines results in thermal packs which have good overall drape characteristics, readily conform with various body forms, and/or have increased structural support of the heat cell matrix.

Because the heat cells are not readily flexible, the spacing between the heat cells provides the preferred benefits and may be determined, when selectively placing the heat cells within or fixed to the unified structure of the thermal packs of the present invention, wherein at least one heat cell of four adjacent heat cells, whose centers form a quadrilateral pattern, blocks one or more axes that could otherwise form at least one fold line tangential to the edges of one or more pairings of the remaining three heat cells in the quadrilateral pattern. Preferably, the spacing between at least one heat cell of the four adjacent heat cells and each of the heat cells of the one or more pairings of the remaining heat cells in the quadrilateral pattern may be calculated using the equation:

$$s \leq (W_q/2)*0.75$$

Where s=the closest distance between the heat cells; and $W_q$=the measurement of the smallest diameter of the smallest diameter heat cell within the quadrilateral pattern.

Alternatively, the spacing between the heat cells may be determined wherein, at least one heat cell of three adjacent heat cells, whose centers form a triangular pattern, blocks one or more axes that could otherwise form at least one fold line tangential to the edges of the remaining pair of heat cells in the triangular pattern formed by the three heat cells. Most preferably, the spacing between the at least one heat cell of the three adjacent heat cells and each heat cell of the remaining pair of heat cells in the triangular pattern may be calculated using the equation:

$$s \leq (W_t/2)*0.3$$

Where s=the closest distance between the heat cells; and $W_t$=the measurement of the smallest diameter of the smallest diameter heat cell within the triangular pattern.

Different materials may be capable of satisfying the above specified requirements. Such materials may include, but are not limited to, those materials mentioned above.

A most preferred embodiment of the disposable thermal packs of the present invention comprises at least one continuous layer of semirigid material having the thermophysical properties described above, and the heat cells fixed within or to the unified structure of the thermal pack in positions relative to each other which are sufficiently close so as to block some or all possible axes across the material of the continuous layer(s), which otherwise would have passed uninterrupted between the heat cells, through the thermal packs, or select regions thereof, to minimize or eliminate undesirable, uninterrupted fold lines, as described above.

Heat Cells

The thermal packs of the present invention comprise a plurality of individual heat cells fixed within or to the unified structure of the thermal pack. These heat cells are spaced apart from each other and each heat cell functions independently of the rest of the heat cells. While the heat cells may comprise any suitable composition providing heat, such as exothermic compositions, microwaveable compositions, heat of crystallization compositions, and the like, the preferred heat cell contains a densely packed, particulate exothermic composition which substantially fills the available cell volume within the cell reducing any excess void volume thereby minimizing the ability of the particulate matter to shift within the cell. Alternatively, the exothermic composition may be compressed into a hard tablet or slug before being placed into each cell.

The preferred exothermic composition comprises a mix of chemical compounds that undergo an oxidation reaction during use. The mix of compounds typically comprises iron powder, carbon, a metal salt(s), and water. Mixtures of this type react when exposed to oxygen, providing heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 μm, preferably less than 150 μm.

The above-mentioned components of the composition are blended using conventional blending techniques. Suitable methods of blending these components are described in detail in U.S. Pat. No. 4,649,895 to Yasuki et al., issued Mar. 17, 1987 which is incorporated by reference herein in its entirety. For example, carbon is added to a blender or mixer, followed by a small amount of the total water and this combination is mixed. Usually enough water is added to assist in blending while avoiding escalated corrosion. Mixing is stopped and vermiculite is added to the carbon. Mixing is resumed until all the components are mixed thoroughly and iron powder is added and mixed. The composition is then blended until thoroughly mixed. Sodium chloride and the remaining water are mixed to form a brine solution which is then added to the particulate composition during construction of the heat cell.

In the alternative, the above-mentioned components of the composition can be blended using conventional blending techniques. For example, carbon is added to a blender or mixer, followed by a small amount of the total water and this combination is mixed. Usually enough water is added to assist in blending while avoiding escalated corrosion. Mixing is stopped and vermiculite and sodium chloride are added to together. Mixing is resumed until all the components are mixed thoroughly and iron powder is added and mixed. The composition is then blended until thoroughly mixed. Additional water is added to the particulate composition during construction of the heat cell.

Alternatively to the above described particulate exothermic composition, the exothermic composition may be formed into agglomerated granules, direct compacted into compaction articles such as granules, pellets, tablets, and/or slugs, and mixtures thereof.

The exothermic composition of these agglomerated granules and/or compaction articles comprises iron powder, dry powdered carbonaceous material, an agglomeration aid, and a dry binder. Additionally, a metal salt, is added to the dry mix or subsequently as an aqueous/brine solution.

As described above for the particulate exothermic composition, there is no particular limitation to the purity, kind, etc. of the iron powder used in the agglomerated granules and/or compaction articles, so long as it can be used to produce heat-generation with electrically conducting water and air. Suitable sources for iron powder include cast iron powder, reduced iron powder, electrolytic iron powder, scrap iron powder, pig iron, wrought iron, various steels, iron alloys, and the like and treated varieties of these iron powders. Typically, the iron powder comprises from about 30% to about 80%, preferably from about 40% to about 70%, most preferably from about 50% to about 65% by weight, of the agglomerated pre-compaction compositions.

Likewise, there is no limitation to the kinds of active carbon used, however, the preferred active carbon has superior water holding capabilities and the different carbons may be blended to reduce cost. Active carbon prepared from coconut shell, wood, charcoal, coal, bone coal, etc. are useful, but those prepared from other raw materials such as animal products, natural gas, fats, oils and resins are also useful in the agglomerated granules and/or compaction articles. Typically, activated carbon, non-activated carbon, and mixtures thereof, comprises from about 3% to about 20%, preferably from about 5% to about 15%, most preferably from about 6% to about 12% by weight, of the agglomerated pre-compaction compositions.

The metal salt is typically added as a dry powder to the exothermic composition before agglomeration, but may also be added to the exothermic compositions in the water as a salt (brine) solution. Metal salts which are useful are the alkali, alkaline earth, and transitional metal salts which includes sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Other suitable alkali, alkaline earth, and transition metal salts also exist which can be used, alone or in combination. Also, carbonate salts, acetate salts, nitrates, nitrites and other salts can be used. Typically, the metal salt(s) comprises from about 0.5% to about 10%, preferably from about 1% to about 8%, most preferably from about 2% to about 6% by weight, of the agglomerated pre-compaction compositions.

Maintaining the content uniformity of powders after mixing and prior to compaction is a primary concern. Therefore, the essential reaction chemistry is agglomerated using low levels of agglomeration aids prior to the addition of dry binders necessary for a hard compaction. Examples of agglomeration aids which are useful, but not limited to, include gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup. The preferred agglomerating aids are crystallizing sorbitol, amorphous sorbitol, corn syrup, maltitol syrup, and mixtures thereof. Typically, agglomeration aids comprise from about 0% to about 9%, preferably from about 0.5% to about 8%, more preferably from about 0.6% to about 6%, most preferably from about 0.7% to about 3% by weight, of the agglomerated pre-compaction compositions.

Since iron and carbon do not compact easily, binders which are capable of binding fine powder under dry conditions and at low concentration while producing a non-friable granulation, must be added to the exothermic compositions. Dry binders which are useful, but not limited to, include maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate. The preferred dry binding agent is microcrystalline cellulose. The amount of dry binder added depends on the degree of hardness desired, however, dry binders typically comprise from about 0% to about 35%, preferably from about 4% to about 30%, more preferably from about 7% to about 20%, most preferably from about 9% to about 15% by weight, of the agglomerated pre-compaction compositions.

The aqueous solution typically used in the compositions comprising agglomerated granules and/or direct compacted articles is water. Water may also serve as a solvent for dissolving and carrier for delivering the metal salt and added in the form of a brine solution. The water used herein may be from any appropriate source. There is no particular limitation to its purity, kind, etc. The amount of aqueous solution added to the exothermic compositions depends on the type and amount of iron to be added, however, the aqueous solution typically, comprises from about 10% to about 50%, preferably from about 15% to about 40%, most preferably from about 15% to about 30%, by weight of the compaction articles.

In addition to the above described components of the agglomerated granules and/or compaction articles, other components may also be added as appropriate. These include additional water-holding materials, disintegrants, lubricants, oxidation is reaction enhancers, compounds to prevent the generation of gases, fillers, anti-caking agents, thickeners, surfactants, and extending agents. Such additional components are previously described herein.

Heat cells comprising agglomerated granules are typically made using conventional blending techniques and agglomerated into granules. For example, powdered carbon and a metal salt are added to a blender or mixer, and blended into a uniform dry mixture. An additional water-holding material is added and the composition is mixed until uniform. For this particular method of making heat cells, dry binders may be optionally added to the composition along with the additional water-holding material. Powdered iron is added and the mixture is again blended until uniform. An agglomeration aid is then added to the blended powders. The composition is mixed until a light agglomeration is formed and no dust appears. The granules may be placed directly into a heat cell pocket or direct compacted into compaction articles. These agglomerated granules are soft, porous, easily wetted, and less dense particles, which may be sufficient in some applications.

Heat cells comprising compaction articles are preferably made by direct compaction of the dry ingredients into articles such as hard granules, pellets, tablets, and/or slugs. For example, powdered carbon and a metal salt are added to a blender or mixer, and blended into a uniform dry mixture. Powdered iron and a disintegrant are added to the carbon/salt mixture and blended until the new mixture is uniform. An agglomeration aid is added to the blended powders. The composition is mixed until a light agglomeration is formed and no dust appears. An additional water-holding material is then added to the agglomeration. Gentle mixing continues until the additional water-holding material is evenly dispersed in the agglomeration. A dry binder is added to the agglomeration and the composition is mixed until uniform. The mixture is then transferred to a rotary tablet press and compressed into disk shaped tablets having a hole passing perpendicular through the middle of the top and bottom surfaces, having concaved top and bottom surfaces, i.e., double whisper design, or other shapes forming a reservoir conducive to holding water.

In a variation of the method described above, the pre-compaction composition may be compressed into a slug, having no particular shape, or a tablet which lacks the hole or reservoir, rather, the tablet comprises any standard tablet configuration including spherical, convexed shallow face, convexed standard face, convexed deep face, flat face, and capsule, flat edge, beveled edge, oval, and modified ball.

Suitable methods of making tablets and/or slugs are described in detail in Chapter 89, "Oral Solid Dosage Forms", Remington's Pharmaceutical Sciences, $18^{th}$ Edition, (1990), pp. 1634–1656, Alfonso R. Gennaro, ed., incorporated herein by reference in its entirety. Any conventional tableting machine and compression pressures, up to the maximum provided by the machine can be used.

Activation of each cell may be accomplished by injecting water or salt solution, i.e., by needle, through the oxygen permeable layer into the hole or reservoir in the middle of the tablet, or into the granular composition. Since the heat cell will begin to generate heat shortly after activation if exposed to air, the thermal pack is placed into an oxygen impermeable secondary package, which may be optionally evacuated of oxygen, and then sealed. Alternatively, water or salt solution can be added to exothermic composition prior to the application of the second continuous layer which forms the heat cell.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The preferred shape of the tablet/slug comprises a disk shaped geometry, having a concaved (whisper) configuration to the top and/or bottom of the tablet. The more preferred shape of the tablet/slug, however, comprises a disk shaped geometry, having a hole perpendicular to, and through the middle of the top and bottom of the tablet.

A water-carrying material having hydrous property and flexibility such as super absorbents, a spongy body, paper, synthetic resin-foam, rubber, cellulose, and the like may be placed in the hole or reservoir to gradually supply the water to the compressed particulate composition to prolong the exothermic reaction.

The size of the compacted disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 1 cm, preferably from about 0.15 cm to about 0.8 cm, more preferably from about 0.2 cm to about 0.6 cm, and most preferably from about 0.2 cm to about 0.5 cm. Alternatively, the compacted disk having a geometric shape other than a disk shape may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from about 0.08 cm to about 1 cm, preferably from about 0.15 cm to about 0.8 cm, more preferably from about 0.2 cm to about 0.6 cm, and most preferably from about 0.2 cm to about 0.5 cm, and a length at its longest point of from about 1.5 cm to about 20 cm, preferably from about 1 cm to about 15 cm, more preferably from about 1 cm to about 10 cm, most preferably from about 3 cm to about 5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are compressed to the hardest possible mechanical strength to withstand the shocks of handling in their manufacture, packing, shipping, and dispensing. The compaction articles are typically compressed to a density of greater than about $1 \text{ g/cm}^3$, preferably from about $1 \text{ g/cm}^3$ to about $3 \text{ g/cm}^3$, more preferably from about $1.5 \text{ g/cm}^3$ to about $3 \text{ g/cm}^3$, and most preferably from about $2 \text{ g/cm}^3$ to about $3 \text{ g/cm}^3$.

Heat cells comprising the above described components are typically formed by adding a fixed amount of a particulate exothermic composition or compaction article(s) to a pocket or pockets made in a first continuous layer. A second continuous layer is placed over the first continuous layer, sandwiching the particulate exothermic composition or compaction article(s) between the two continuous layers which are then bonded together, preferably using low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

Pockets are typically made in the first continuous layer by thermoforming, mechanical embossing, vacuum embossing, or other acceptable means. A preferred method for use herein is thermoforming which is described in "Thermoforming",

*The Wiley Encyclopedia of Packaging Technology*, pp. 668–675 (1986), Marilyn Bakker, ed., incorporated herein by reference in its entirety. Typically, the first continuous layer is placed on a mold having a plurality of appropriately-shaped indentations spaced apart. The first continuous layer is then heated and a vacuum is applied such that the first continuous layer is drawn into and conforms to the mold. The particulate composition or compaction article(s) is placed on top of the first continuous layer directly into the heat/vacuum-formed pocket(s). As the particulate composition or compaction article(s) is dropped into the pocket(s), it may be held in place by gravity, vacuum, and/or a magnetic force in the bottom of the mold indentation. The second continuous layer is then placed over the first continuous layer, such that the particulate composition or compaction article(s) is between the two continuous layers. The particulate composition or compaction article(s) is sealed between the first and second continuous layers, preferably using a low heat, and the vacuum is removed.

A more preferred method of preparing individual heat cells uses vacuum only to form the pockets. That is, vacuum is used to draw the first continuous layer to a mold having a plurality of appropriately-shaped indentations spaced apart. The particulate composition or compaction article(s) is placed on top of the first continuous layer directly into the vacuum-molded pocket(s). As the particulate composition or compaction article(s) is dropped into the vacuum formed pocket(s), it is held in place by gravity, vacuum, and/or a magnetic force in the bottom of the mold indentation. The second continuous layer is then placed over the first continuous layer, such that the particulate composition or compaction article(s) is between the two continuous layers. The particulate composition or compaction article(s) is sealed between the first and second continuous layers, preferably using low heat. The vacuum is then removed, allowing the first continuous layer to form a tightly packed heat cell(s).

The heat cells may also be prepared by using magnetic transfer of a fixed amount of the particulate exothermic composition to the pockets as described in Japanese Kokoku Patent No. HEI 05/081261 to Watabe, et al., issued Jan. 7, 1992, which is incorporated herein by reference in its entirety.

The finished heat cell can have any geometric shape, e.g., disk, triangle, pyramid, cone, sphere, square, cube, rectangle, rectangular parallelepiped, cylinder, ellipsoid and the like. The preferred shape of the heat cells manufactured according to the present invention, comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells manufactured according to the present invention have a height of from greater than about 0.2 cm to about 1 cm, preferably from greater than about 0.2 cm to about 0.9 cm, more preferably from greater than about 0.2 cm to about 0.8 cm, and most preferably from about 0.3 cm to about 0.7 cm. Alternatively, the heat cells having geometric shapes other than a disk shape, preferably an ellipsoid (oval), may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from greater than about 0.2 cm to about 5 cm, preferably from greater than about 0.2 cm to about 1 cm, more preferably from greater than about 0.2 cm to about 0.8 cm, and most preferably from about 0.3 cm to about 0.7 cm, and a length at its longest point of from about 0.5 cm to about 20 cm, preferably from about 1 cm to about 15 cm, more preferably from about 1 cm to about 10 cm, most preferably from about 3 cm to about 5 cm.

The ratio of fill volume to cell volume is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability can be provided by selecting materials for the first and second continuous layers forming the pockets, and/or covering layer, that have the specifically desired permeability properties. The desired permeability properties may be provided by microporous films or by films which have pores or holes formed therein. The formation of holes/pores may be via extrusion cast/vacuum formation or by hot or cold needle aperturing. For example, at least one of the continuous layers described above may be apertured prior to heat cell construction. This aperturing is preferably achieved via the use of an array of hot needles having tapered points and base diameters of from about 0.2 mm to about 2 mm, preferably from about 0.4 mm to about 1.5 mm, more preferably from about 0.8 mm to about 1.0 mm, and a length of about 6 mm. These needles are heated to a temperature of from about 90° C. to about 400° C. and pierce the material to a depth of from about 200 $\mu$m to about 500 $\mu$m. A needle density of from about 2 to about 30 pins per square centimeter, preferably from about 4 to about 10 needles per square centimeter provides the desired permeability properties which control the rate of the chemical oxidation and hence the thermal output of the heat cells.

Oxygen permeability can also be provided in the present invention after the continuous layers have been bonded together enclosing the exothermic composition in the pocket between them, by perforating one side of the heat cells with aeration holes using, for example, at least one pin, preferably an array of from about 20 to about 60 pins having tapered points and diameters of from about 0.2 mm to about 2 mm, preferably from about 0.4 mm to about 0.9 mm. The pins are pressed through one side of the continuous layer material to a depth of from about 2% to about 100%, preferably from about 20% to about 100%, and more preferably from about 50% to about 100% into the particulate exothermic composition.

These hole configurations typically provide an oxygen diffusion into the heat cell during oxidation of the exothermic composition of from about 0.01 cc $O_2$/min./5 cm$^2$ to about 15.0 cc $O_2$/min./5 cm$^2$ (at 21° C., 1 ATM), preferably from about 0.9 cc $O_2$/min./5 cm$^2$ to about 3 cc $O_2$/min./5 cm$^2$ (at 21° C., 1 ATM). Although there is preferably provided aeration holes in the upper covering continuous layer, it is also possible to provide aeration holes in the lower continuous layer, and/or both.

The velocity, duration, and temperature of the thermogenic oxidation reaction of the particulate exothermic composition can be controlled as desired by changing the area of contact with air, more specifically, by changing the oxygen diffusion/permeability.

In a preferred embodiment, the thermal packs of the present invention consist of at least one continuous layer of a material which exhibits the thermophysical characteristics specified herein. Continuous layer or layers of one or more such materials are typically included as one or both of the layers used to form the heat cells. Alternatively, the heat cells may be mounted individually or in one or more groups to one or more continuous layers of a material which exhibits the thermophysical characteristics specified herein.

The thermal packs of the present invention may optionally incorporate a component, such as a separate substrate layer or incorporated into at least one of the continuous layers, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof. The thermal pack may also comprise a separate substrate layer, or incorporated into at least one of the continuous layers, a self-adhesive component and/or a sweat-absorbing component.

The thermal packs of the present invention may comprise any number of sizes and/or shapes, as appropriate, and may be used alone or can be incorporated into various wraps or pads. Typically, these wraps have a means for retaining wraps or pads in place around various parts of the body, such as knee, neck, back, abdomen, and the like, and can comprise any number of styles and shapes.

The finished thermal packs are typically packaged in a secondary package. An air-impermeable package may be used to prevent an oxidation reaction from occurring until desired as described in the aforementioned U.S. Pat. No. 4,649,895, already incorporated herein by reference in its entirety. Alternatively, other means may also be used to prevent an oxidation reaction from occurring before desired, such as air impermeable removable adhesive strips can be placed over the aeration holes in the heat cells such that, when the strips are removed, air is allowed to enter the heat cell, thus activating the oxidation reaction of the iron powder.

The present invention further comprises a method for treating acute, recurrent, and/or chronic pain, including skeletal, muscular, and/or referred pain, by topically applying heat to the afflicted body part of a person suffering such pain. The method comprises maintaining a skin temperature to the afflicted area of from about 32° C. to about 50° C., preferably from about 32° C. to about 45° C., more preferably from about 32° C. to about 42° C., most preferably from about 32° C. to about 39° C., still most preferably from about 32° C. to about 37° C., preferably by applying the disposable thermal pack or packs of the present invention to the afflicted area, for from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved, without any adverse events, such as skin burns which may be incurred by using a high temperature for a long period of time.

Preferably the method comprises maintaining a sustained skin temperature of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, to substantially relieve acute, recurrent, and/or chronic pain, including skeletal, muscular, and/or referred pain, of a person having such pain and to substantially prolong relief, for at least about 2 hours, preferably for at least about 8 hours, more preferably for at least about 16 hours, most preferably for at least about one day, still most preferably for at least about three days, from such pain, even after the heat source is removed from the afflicted body part.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal pack having a unified structure comprising:
   a.) at least one continuous layer of a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C.; and
   b.) a plurality of individual heat cells, spaced apart and placed into positions fixed within said unified structure of said thermal pack or to said at least one continuous layer of said semirigid material.

2. A disposable thermal pack according to claim 1 wherein said at least one continuous layer comprises a tensile strength of about 0.85 g/mm$^2$, or greater, and at least two-dimensional drape at a temperature of about 25° C.

3. A disposable thermal pack according to claim 2 wherein said at least one continuous layer comprises a tensile strength of about 1 g/mm$^2$, or greater, and at least two-dimensional drape at a temperature of about 25° C.

4. A disposable thermal pack according to claim 1 wherein said at least one continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

5. A disposable thermal pack according to claim 4 wherein said at least one continuous layer comprises an extruded material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer.

6. A disposable thermal pack according to claim 5 wherein said at least one continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

7. A disposable thermal pack according to claim 6 wherein said at least one continuous layer comprises a coextruded material having a first side of polypropylene and a second side of ethylene-vinyl acetate copolymer.

8. A disposable thermal pack according to claim 7 wherein said at least one continuous layer comprises a coextruded material having a first side of polypropylene and a second side of ethylene vinyl acetate copolymer, wherein said polypropylene comprises from about 10% to about 90% of the total thickness of said material.

9. A disposable thermal pack according to claim 8 wherein said at least one continuous layer comprises a coextruded material having a first side of polypropylene and a second side of ethylene vinyl acetate copolymer, wherein said polypropylene comprises from about 40% to about 60% of the total thickness of said material.

10. A disposable thermal pack according to claim 1 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein further said heat cells, when filled with an exothermic composition, have a fill volume to cell volume ratio of from about 0.7 to about 1.0.

11. A disposable thermal pack according to claim 10 wherein said exothermic composition comprises:
  a.) from about 30% to about 80% by weight, iron powder;
  b.) from about 3% to about 25% by weight, carbonaceous material selected from the group consisting of activated carbon, non-activated carbon, and mixtures thereof;
  c.) from about 0.5% to about 10% by weight, metal salt; and
  d.) from about 1% to about 40% by weight, water.

12. A disposable thermal pack according to claim 11 wherein said exothermic composition further comprises from about 0.1% to about 30% by weight, of additional water-holding material.

13. A disposable thermal pack according to claim 10 wherein said exothermic composition comprises:
  a.) from about 30% to about 80% by weight, of iron powder;
  b.) from about 3% to about 20% by weight, of carbonaceous material selected from the group consisting of activated carbon, non-activated carbon, and mixtures thereof, and
  c.) from about 0.5% to about 9% by weight, of an agglomeration aid selected from the group consisting of corn syrup, maltitol syrup, crystallizing sorbitol syrup, amorphous sorbitol syrup, and mixtures thereof;
  wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

14. A disposable thermal pack according to claim 13 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

15. A disposable thermal pack according to claim 13 wherein said dry binder comprises from about 4% to about 30% by weight, of microcrystalline cellulose.

16. A disposable thermal pack according to claim 13 wherein said tablets comprise a geometric shape selected from the group consisting of a disk shape having a hole passing perpendicular to and through the middle of the top and bottom surfaces and a disk shape wherein said top and bottom surfaces are concaved forming a reservoir conducive to holding a liquid.

17. A disposable thermal pack according to claim 13 wherein said direct compaction articles comprise a density of greater than about 1 g/cm$^3$.

18. A disposable thermal pack according to claim 1 further comprising additional components selected from the group consisting of active aromatic compounds, non-active aromatic compounds, pharmaceutical actives, and mixtures thereof.

19. A disposable thermal pack having a unified structure comprising at least one continuous layer of material and a plurality of individual heat cells placed into positions fixed within or to said unified structure of said thermal pack, which are sufficiently close and relative to each other, so as to block some or all possible axes across said at least one continuous layer, which otherwise would have passed uninterrupted between said heat cells, through said thermal pack, or select regions thereof.

20. A disposable thermal pack according to claim 19 wherein at least one of said heat cells of four adjacent said heat cells, whose centers form a quadrilateral pattern, blocks one or more of said axes that could otherwise form at least one fold line tangential to the edges of one or more pairings of the remaining said heat cells in the quadrilateral pattern.

21. A disposable thermal pack according to claim 20 wherein the spacing between said at least one of said heat cells and each of said heat cells of said one or more pairings of said remaining heat cells in said quadrilateral pattern is the same or less than the spacing obtained by dividing the measurement of the smallest diameter of the smallest diameter heat cell of said heat cells within said quadrilateral pattern by 2 and multiplying the result by 0.75.

22. A disposable thermal pack according to claim 19 wherein at least one of said heat cells of three adjacent said heat cells, whose centers form a triangular pattern, blocks one or more of said axes that could otherwise form at least one fold line tangential to the edges of the remaining pair of said heat cells in the triangular pattern formed by said three heat cells.

23. A disposable thermal pack according to claim 22 wherein the spacing between said at least one of said heat cells and each of said heat cells of said remaining pair of said heat cells in said triangular pattern is the same or less than the spacing obtained by dividing the measurement of the smallest diameter of the smallest diameter heat cell of said heat cells within said triangular pattern by 2 and multiplying the result by 0.3.

24. A disposable thermal pack according to claim 19 wherein said at least one continuous layer comprises a semirigid material having a tensile strength of about 0.7 g/mm², or greater, and at least two-dimensional drape at a temperature of about 25° C., and wherein said material has a tensile strength, at a temperature of about 35° C. or greater, substantially less than said tensile strength of said material at about 25° C.

25. A disposable thermal pack according to claim 24 wherein said continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

26. A disposable thermal pack according to claim 25 wherein said continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

27. A disposable thermal pack according to claim 26 wherein said continuous layer comprises a coextruded material having a first side of polypropylene and a second side of ethylene-vinyl acetate copolymer.

28. A disposable thermal pack according to claim 19 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein said heat cells, when filled with an exothermic composition, have a fill volume to cell volume ratio of from about 0.7 to about 1.0.

29. A disposable thermal pack according to claim 28 wherein said exothermic composition comprises:
 a.) from about 30% to about 80% by weight, iron powder;
 b.) from about 3% to about 25% by weight, carbonaceous material selected from the group consisting of activated carbon, non-activated carbon, and mixtures thereof,
 c.) from about 0.5% to about 10% by weight, metal salt; and
 d.) from about 1% to about 40% by weight, water.

30. A disposable thermal pack according to claim 29 wherein said exothermic composition further comprises from about 0.1% to about 30% by weight, of additional water-holding material.

31. A disposable thermal pack according to claim 28 wherein said exothermic composition comprises:
 a.) from about 30% to about 80% by weight, of iron powder;
 b.) from about 3% to about 20% by weight, of carbonaceous material selected from the group consisting of activated carbon, non-activated carbon, and mixtures thereof; and
 c.) from about 0.5% to about 9% by weight, of an agglomeration aid selected from the group consisting of corn syrup, maltitol syrup, crystallizing sorbitol syrup, amorphous sorbitol syrup, and mixtures thereof;
 wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

32. A disposable thermal pack according to claim 31 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

33. A disposable thermal pack according to claim 31 wherein said dry binder comprises from about 4% to about 30% by weight, of microcrystalline cellulose.

34. A disposable thermal pack according to claim 31 wherein said tablets comprise a geometric shape selected from the group consisting of a disk shape having a hole passing perpendicular to and through the middle of the top and bottom surfaces and a disk shape wherein said top and bottom surfaces are concaved forming a reservoir conducive to holding a liquid.

35. A disposable thermal pack according to claim 31 wherein said direct compaction articles comprise a density of greater than about 1 g/cm³.

36. A disposable thermal pack according to claim 19 further comprising additional components selected from the group consisting of active aromatic compounds, non-active aromatic compounds, pharmaceutical actives, and mixtures thereof.

37. A disposable thermal pack according to claim 13 further comprising from about 4% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof.

38. A disposable thermal pack according to claim 31 further comprising from about 4% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof.

* * * * *